(12) United States Patent
Kuhn et al.

(10) Patent No.: US 6,462,203 B2
(45) Date of Patent: Oct. 8, 2002

(54) PROCESS FOR THE PREPARATION OF DIHYDROCOUMARIN BY HYDROGENATING COUMARIN

(75) Inventors: Walter Kuhn, Holzminden (DE); Hans-Ulrich Funk, Lauenförde (DE); Gerhard Senft, Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/941,078

(22) Filed: Aug. 28, 2001

(65) Prior Publication Data

US 2002/0049340 A1 Apr. 25, 2002

(30) Foreign Application Priority Data

Sep. 1, 2000 (DE) .......................................... 10043094

(51) Int. Cl.$^7$ ............................................ C07D 311/20
(52) U.S. Cl. ..................................................... 549/290
(58) Field of Search ......................................... 549/290

(56) References Cited

U.S. PATENT DOCUMENTS 3,442,910 A    5/1969    Thweatt ................... 260/343.2
5,237,075 A    8/1993    Shirafuji et al. ............. 549/290

OTHER PUBLICATIONS

Kokotos, George and Chrysa Tzougraki, Synthesis and Study of Substituted Coumarins. A Facile Preparation of D,L–o–Tryrosine, (1996), Journal of Heterocyclic Chemistry, vol. 23, No. 1, pp. 87–92.*

Huck et al., Potential and Limitations of Palladium–Cinchona Catalyst for the Enantioselective Hydrogenation of a Hydroxymethylpyrone, (Jul. 1, 2000), Journal of Catalysis, vol. 193, No. 1, pp 1–4.*

Babiker et al., A Simple Flow Reactor For Transfer Hydrogenation of Olefins, Tetrahedron Letters, vol. 29, No. 44, pp. 5599–5600, 1988.*

J. Am. Chem. Soc. 62, Feb. 1940, pp. 283–287, Peter L. de Benneville and Ralph Connor, The Hydrogenation of Coumarin and Related Compounds.

Perfume and Flavour Chemicals, S. Arctander, (Month unavailable) 1969, No. 934 Dihydrocoumarin.

* cited by examiner

Primary Examiner—Joseph K. McKane
Assistant Examiner—Rebecca Anderson
(74) Attorney, Agent, or Firm—Joseph C. Gil; Noland J. Cheung

(57) ABSTRACT

Dihydrocoumarin is prepared by hydrogenating coumarin in the presence of a palladium catalyst.

4 Claims, No Drawings

PROCESS FOR THE PREPARATION OF DIHYDROCOUMARIN BY HYDROGENATING COUMARIN

FIELD OF THE INVENTION

The invention relates to a process for the preparation of dihydrocoumarin by hydrogenating coumarin in the presence of a palladium catalyst.

BACKGROUND OF THE INVENTION

J. Am. Chem. Soc., 62, 1940, 283–287 describes the hydrogenation of coumarin to dihydrocoumarin under Raney nickel catalysis at 100° C. The hydrogenation is carried out in diethyl ether at a pressure of 100 bar and, following distillation, gives dihydrocoumarin in a 90% yield.

U.S. Pat. No. 3,442,910 describes the preparation of dihydrocoumarin and derivatives by dehydrogenating and cyclizing 2-oxocyclohexanepropionic acid in the presence of platinum, palladium, nickel, rhodium or ruthenium catalyst. For this reaction, temperatures of from 275 to 325° C. are required. The solvent used is preferably diphenyl ether. The yield of dihydrocoumarin is 60%.

Likewise, EP A 0420532 describes the preparation of dihydrocoumarin starting from 2-oxocyclohexanepropionic acid in the presence of platinum, palladium, nickel, rhodium or iridium catalyst by dehydrogenation and cyclization.

The coumarin, which is formed as a byproduct is converted to dihydrocoumarin in an 87% yield using a palladium catalyst, which has been activated beforehand with atmospheric oxygen, at 80 to 160° C. and a hydrogen pressure of 2 bar.

Dihydrocoumarin can only be prepared by the known processes with an unsatisfactory yield. The reaction conditions, such as high temperatures, high pressures and handling of atmospheric oxygen can only be carried out on an industrial scale with considerable technical complexity.

SUMMARY OF THE INVENTION

It was an object of the present invention to prepare dihydrocoumarin in high purity and good yield in an economical manner. We have found a process for the preparation of dihydrocoumarin by hydrogenating coumarin, wherein palladium, without oxygen activation, is used as the catalyst, and coumarin is hydrogenated at temperatures of <80° C.

DETAILED DESCRIPTION OF THE INVENTION

The process according to the invention is preferably carried out without the use of an additional solvent.

Palladium catalysts are known per se (Methoden der organischen Chemie [Methods of Organic Chemistry]/ Houben Weyl, Volume IV/1c, Reduktion Teil 1 [Reduction Part 1], Georg Thieme Verlag, Stuttgart, 1980, pages 15 to 562, Handbook of Heterogeneous Catalysis, Vol. 1–5, pages 2123 to 2447; VCH Weinheim; 1997).

The catalysts are usually applied to a support. Suitable supports are, for example, activated carbon, silicon dioxide, calcium carbonate or aluminum oxide. The preferred support is activated carbon.

The support for the process according to the present invention generally comprises 1 to 20% by weight, preferably 5 to 10% by weight, of palladium, based on the dry overall catalyst.

For the process according to the present invention, the catalyst can be used in the dry or moist state (up to 60% water).

For the process according to the present invention, the weight ratio of the catalyst used to coumarin is 0.0001 to 0.1:1, preferably 0.005 to 0.5:1.

The reaction temperature for the process according to the present invention is 30 to 80° C., preferably 75° C. to 65° C.

The hydrogen pressure is 1 to 100 bar, preferably 5 to 10 bar.

The reaction time is 2 to 100 hours, preferably 5 to 40 hours.

The process according to the invention can be represented by the following reaction equation:

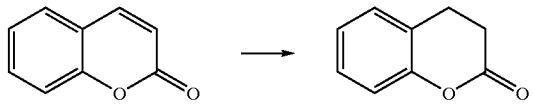

The process according to the invention is generally carried out as follows:

Coumarin and the catalyst are charged to a pressurized container fitted with stirrer. Hydrogenation is carried out at the chosen reaction temperature and hydrogen pressure. The resulting dihydrocoumarin is obtained following removal of the catalyst by filtration, decantation or centrifugation.

The process according to the invention produces dihydrocoumarin in a purity of 99.9% and a yield of 98%.

Dihydrocoumarin is a fragrance with a sweet-herbaceous character reminiscent of hay. (S. Arctander, Perfume and Flavour Chemicals, No. 934, 1969).

EXAMPLE

A 5 l stirred autoclave with gas-dispersion stirrer is charged with 1 500 g of coumarin and 6 g of 5% by weight palladium on activated carbon (moist). Hydrogenation is carried out for 8 hours at 75 to 65° C. and 5 bar. Filtration gives 1 492 g of dihydrocoumarin with a purity of 99.9%. The resulting dihydrocoumarin can be distilled without residue at a still temperature of 140° C. and a vacuum of 3 mbar. The theoretical yield is 98%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of dihydrocoumarin comprising the step of hydrogenating coumarin, wherein palladium without oxygen activation is used as catalyst, and coumarin is hydrogenated at temperatures of <80° C., wherein said process is carried out without the use of an additional solvent.

2. A process according to claim 1, wherein the weight ratio of the catalyst used to coumarin is 0.0001 to 0.1:1.

3. A process according to claim 1, wherein the reaction temperature is in the range from 30 to 80° C.

4. A process according to claim 1, wherein the process is carried out at a hydrogen pressure from 1 to 100 bar.

* * * * *